(12) United States Patent
Levin et al.

(10) Patent No.: US 6,168,606 B1
(45) Date of Patent: Jan. 2, 2001

(54) SINGLE-USE LANCET DEVICE

(75) Inventors: Paul D. Levin, Santa Cruz; John D. Harding, Ben Lomond, both of CA (US); Lance G. Decker, Seagrove, NC (US)

(73) Assignee: Palco Labs, Inc., Santa Cruz, CA (US)

( * ) Notice: Under 35 U.S.C. 154(b), the term of this patent shall be extended for 0 days.

(21) Appl. No.: 09/437,992

(22) Filed: Nov. 10, 1999

(51) Int. Cl.⁷ .................................................. A61B 17/14

(52) U.S. Cl. ............................................ 606/181; 606/182

(58) Field of Search .................................... 606/181, 182, 606/183, 184, 188, 189; 604/192, 198

(56) References Cited

U.S. PATENT DOCUMENTS 4,889,117 * 12/1989 Stevens .................................. 606/181
4,994,068 *  2/1991 Hufnagle .............................. 606/181

* cited by examiner

Primary Examiner—Michael Buiz
Assistant Examiner—Anthony S. King
(74) Attorney, Agent, or Firm—Bruce H. Johnsonbaugh (57) ABSTRACT

A single-use, spring driven lancet is described. The device is precooked during assembly so that the user needs only to remove the safety cap prior to use. A concave trigger button with direct up and down motion releases the spring, causing the tip of the lancet to strike the subject's finger. A thin plastic fiber connection between the pull-tab and the needle safety cap prevents any compressive force from being applied to the drive spring, which effectively prevents recocking of the device.

11 Claims, 9 Drawing Sheets

SINGLE-USE LANCET DEVICE

BACKGROUND AND SUMMARY OF THE INVENTION

Single-use lancets for drawing capillary blood reduce the risk of HIV, hepatitis and other bloodborne diseases. Typically, the needle of these devices is driven into the patient's skin by a small spring which is cocked by the technician just prior to use. The safety cap with its attachment keeps the end of the lancet sterile and, since it can be used as a kind of pushrod, it is also employed by the user to cock the device. When pulled off, the needle is exposed and the device, having been cocked, is ready for use. Such a device is described in U.S. Pat. No. 5,487,748 to Marshall.

A disadvantage of the Marshall device is the ease with which it can be recocked using the same pushrod-type needle cap. The needle cap can simply be replaced over the end of the lancet and pushed inward to once again cock the spring of the lancet. While such an action is unlikely by a professional blood drawer, it is nevertheless an undesirable feature of a lancet constructed in this fashion.

The safety cap of the present invention positively cannot be used to recock a spring-driven lancet. The safety cap to be described uses a thin plastic fiber to pull off the needle cap and because of its flexibility no significant compressive force can be exerted through it to cock the device. In this design, the spring is cocked during assembly before closure of the case. A precooked device is preferable from the point of view of the user because it avoids the necessity of pushing in a pushrod to cock the lancet, therefore saving time and avoiding repetitious pressure against the user's finger. If the device is indeed precooked during the manufacturing process, the trigger mechanism must be secure enough to avoid accidental firing, especially during shipping and handling. In a precooked lancet device, plastic creep can be a problem so construction must be rugged enough to withstand over time the considerable pressure of the cocked spring.

Ideally, the trigger should be comfortable to the user's hand and should be intuitive in its use. To keep costs low, the trigger should be preferably molded with the body of the device so that no separate parts are required.

The trigger for a spring-driven lancet may be at the end of the device as described by Sullivan in U.S. Pat. No. 5,147,375 or Crossman in U.S. Pat. No. 5,100,427. A second method, in which the trigger is pinched between the thumb and index finger, is described in 5,487,748. In the relatively flat Marshall device, the trigger has a rocker-like action and projects 5 to 6 millimeters above the body, making it prone to accidental firing.

The trigger mechanism of the present invention has an up and down motion and is formed as a part of the body which reduces cost. There is a comfortable concave shape to its upper surface for the tip of the finger, and it projects only about a millimeter above the general surface of the body to reduce the risk of accidental triggering. The contact surfaces are fairly broad, which reduces the problem of long-term plastic creep if it is stored in the cocked position. The design has been optimized for an automatic assembly process so that, when the trigger is made as part of the clamshell body, closure of the body will always correctly align the top and bottom halves of the trigger.

A primary object of the invention is to provide a single-use lancet device having a removable safety cap protecting the needle tip wherein the safety cap cannot be utilized to recock and reuse the lancet device.

A further object of the invention is to provide a pre-cocked single-use lancet device.

Another object of the invention is to provide a single-use precooked lancet device with a rugged trigger design which prevents accidental firing of the device during shipping and handling.

Another object of the invention is to provide a single-use lancet capable of using a chisel tip needle for pediatric use.

Other objects and advantages will become apparent from the following description and drawings, wherein:

DETAILED DESCRIPTION OF THE DRAWINGS

Figure 1:
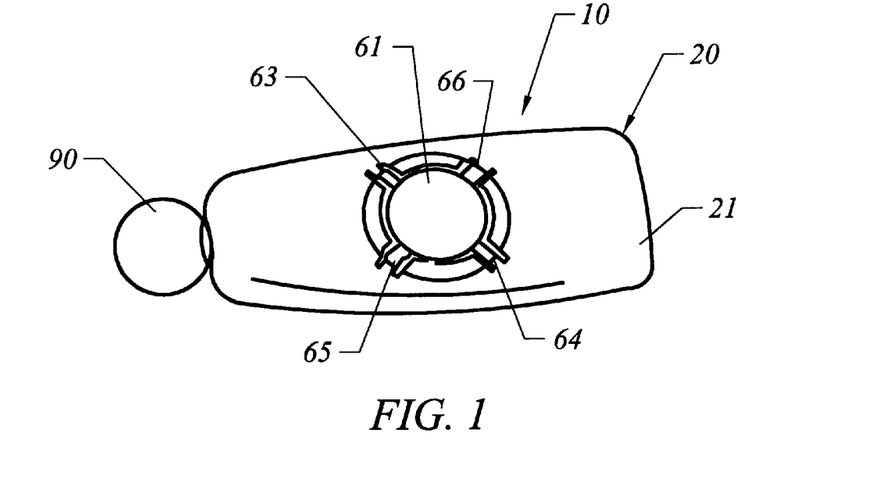
FIG. 1 is a perspective view showing the single-use lancet device of the present invention.

FIG. 1 shows the single-use lancet generally as 10 which has either a trapezoidal or elliptically shaped body 20. A trigger button 61 is molded into the upper half 21 of the body 20 and is capable of direct up and down motion. A pull-tab 90 extends outwardly from body 20. Pull-tab 90 is connected to a safety cap described below which covers the needle tip. The user manipulates pull-tab 90 to prepare the lancet 10 for use in drawing a blood sample.

Figure 2:
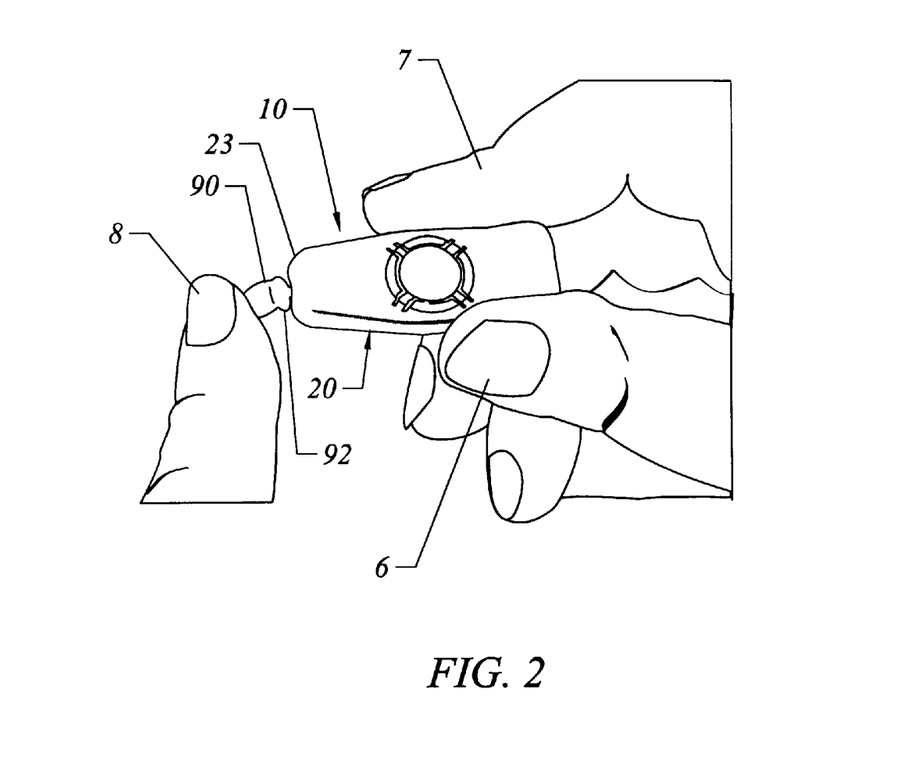
FIG. 2 is a perspective view showing the lancet being held in a user's right hand and showing the pull-tab being manipulated.

FIG. 2 shows the lancet 10 being prepared for use. The user holds the body 20 of the lancet between his or her thumb 6 and forefinger 7 of the right hand and presses pull-tab 90 sideways against the forward end 23 of body 20 with one finger 8 of the left hand. By so manipulating the pull-tab 90 as shown in FIG. 2, the user separates the safety cap described below from the needle assembly.

Figure 3:
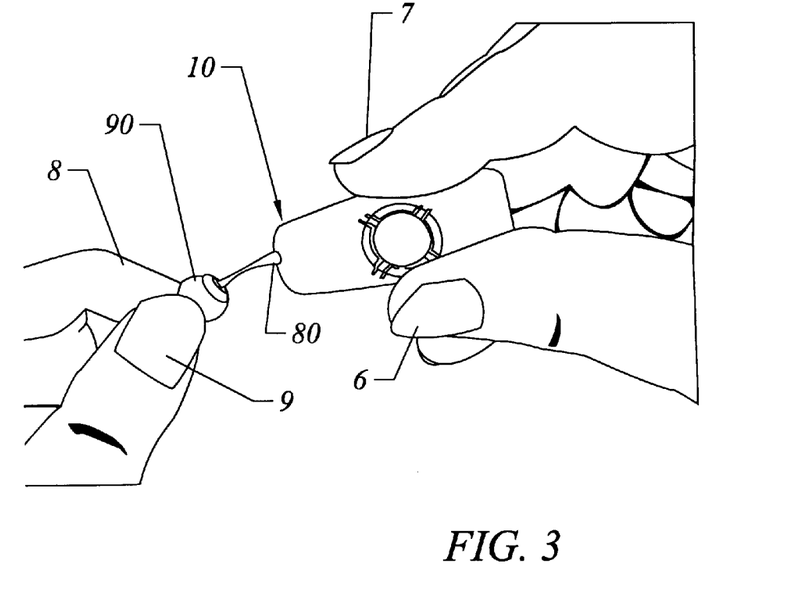
FIG. 3 is a perspective view showing the lancet being held in a user's right hand and the pull-tab being removed by the user's left hand.

FIG. 3 shows the next step in preparation for use of the lancet 10. The user continues to hold the lancet 10 between his or her thumb 6 and forefinger 7 and grasps the pull-tab 90 between the left forefinger 8 and left thumb 9 and simply pulls the pull-tab 90 and safety cap 80 off the lancet 10 and discards the pull-tab 90 and safety cap 80.

Figure 4:
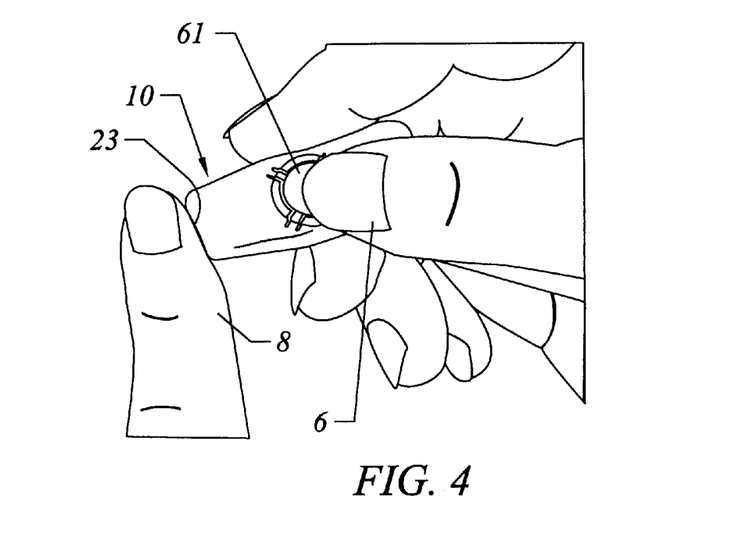
FIG. 4 is a perspective view showing a user applying the lancet to a finger of the left hand and wherein the user is about to depress the trigger with the thumb of the right hand.

FIG. 4 shows the user drawing blood with lancet 10. After the pull-tab has been discarded, the user places the forward end 23 of the lancet against a finger 8 and depresses the trigger button 61 with his or her thumb 6. As described below, the needle assembly is released from its cocked position and moves forward, striking the finger 8 and a blood sample can be taken from the site of the puncture.

Figure 5:
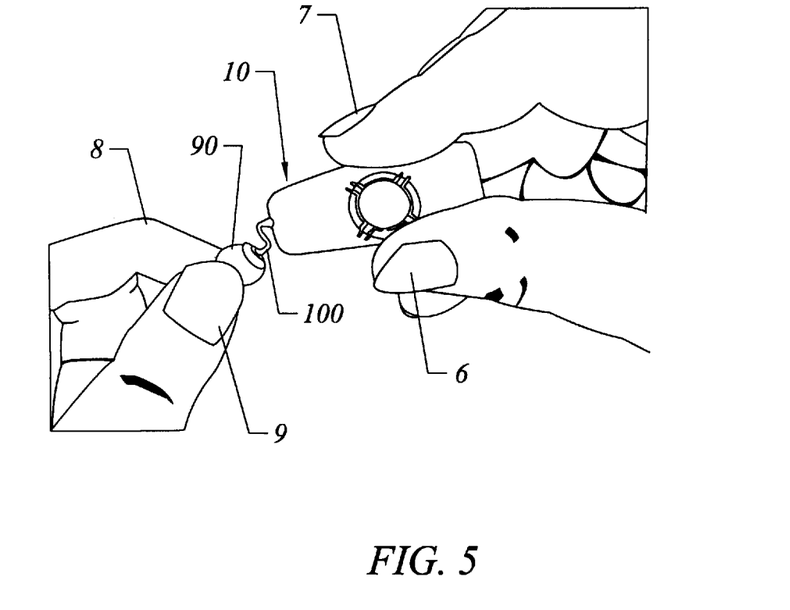
FIG. 5 is a perspective view showing that the user is unable to recock the device because of the flexibility of the thin plastic connector between the pull-tab and the safety cap.
Figure 6:
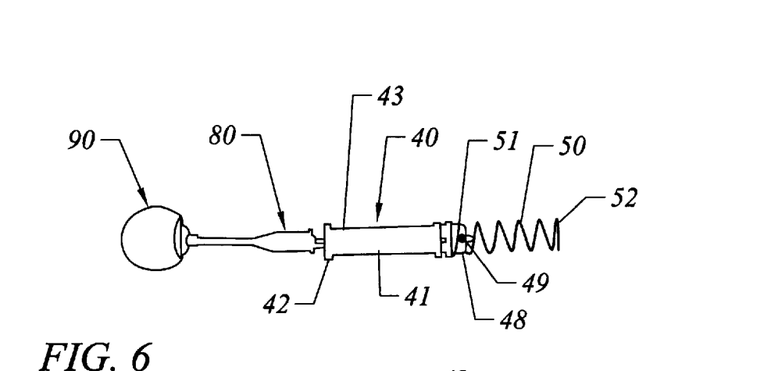
FIG. 6 is a side elevational view showing the pull-tab and safety cap assembly and the needle assembly of the present invention.

FIG. 5 shows a significant feature of the present invention which is the inability to recock the lancet 10 by attempting to reinsert the safety cap (not visible in FIG. 5) and recocking the needle assembly by pushing on pull-tab 90. A thin plastic fiber connection 100 extends between pull-tab 90 and safety cap 80 (FIG. 6). The fiber connector 100 is sufficiently thin and sufficiently flexible that it is unable to provide an effective compressive force to recock the needle assembly. This feature is significant in that reuse by a user or sharing of the lancet 10 between multiple users can and does pose serious health risks.

FIG. 6 shows the needle assembly 40 and how it is attached to the safety cap 80 and pull-tab 90. Needle assembly 40 includes a plastic lancet carrier or needle support 41 which is generally cylindrical in nature and includes a round collar or flange 42 formed at the forward end 43 of carrier 41.

Figure 7:
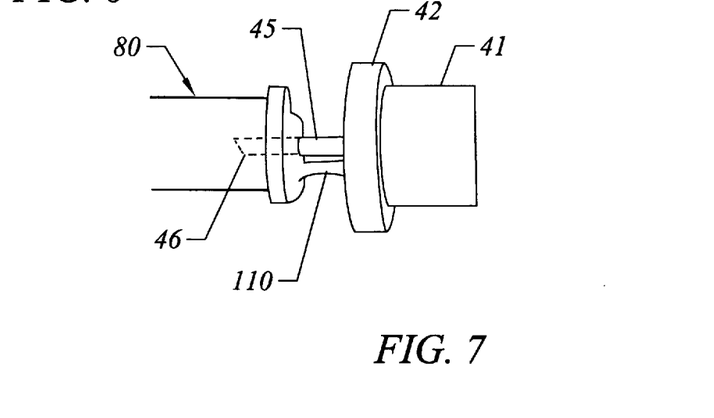
FIG. 7 is an elevational view of a portion of the invention shown in FIG. 6.

FIGS. 6 and 7 show in greater detail how the safety cap 80 is connected to needle assembly 40. Needle 45 is embedded in carrier 41 as is well-known in the art. The tip 46 of needle 45 is shown in phantom in FIG. 7 and is enclosed by safety cap 80. Enclosing the tip 46 of needle 45 in this manner assures sterility of the needle. In order to prevent accidental removal of safety cap 80, a plastic connector 110 is formed between carrier 41 and safety cap 80. Connector 110 prevents accidental loosening of the pull-tab during shipment and handling but is thin enough (0.020 inch) to be easily broken when the cap is deliberately removed by the user. The base end 48 of carrier 41 is connected to drive spring 50. The forward end 51 of drive spring 50 is slid over the base 48 of carrier 41. A lug 49 formed in the base 48 of carrier 41 catches the forward end 51 of the spring 50. The base end 52 of spring 50 engages a seat (FIG. 10) 24 formed in the lower half 22 of the body 20.

Figure 8:
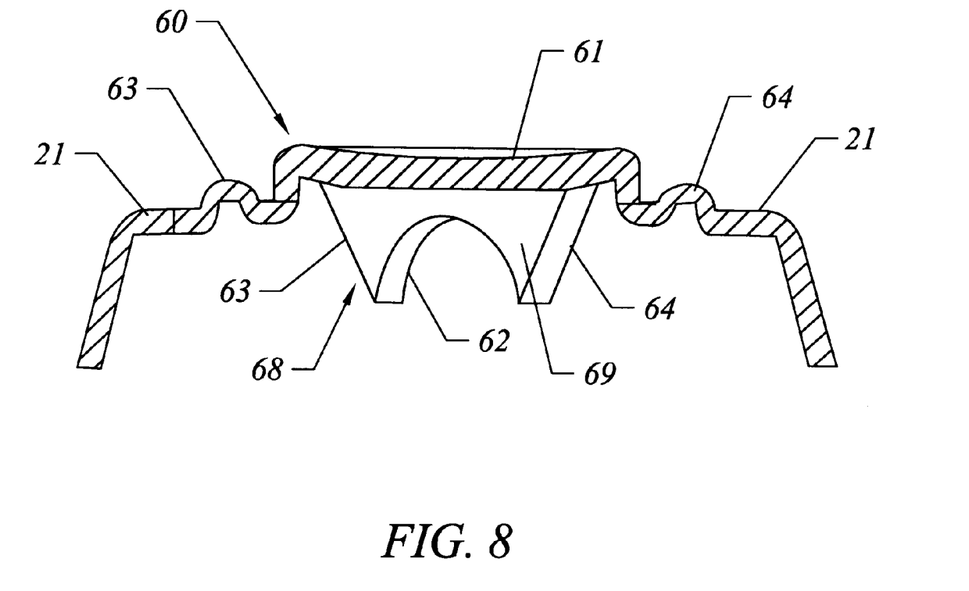
FIG. 8 is a schematic representation showing the trigger button before the trigger is depressed.
Figure 9:
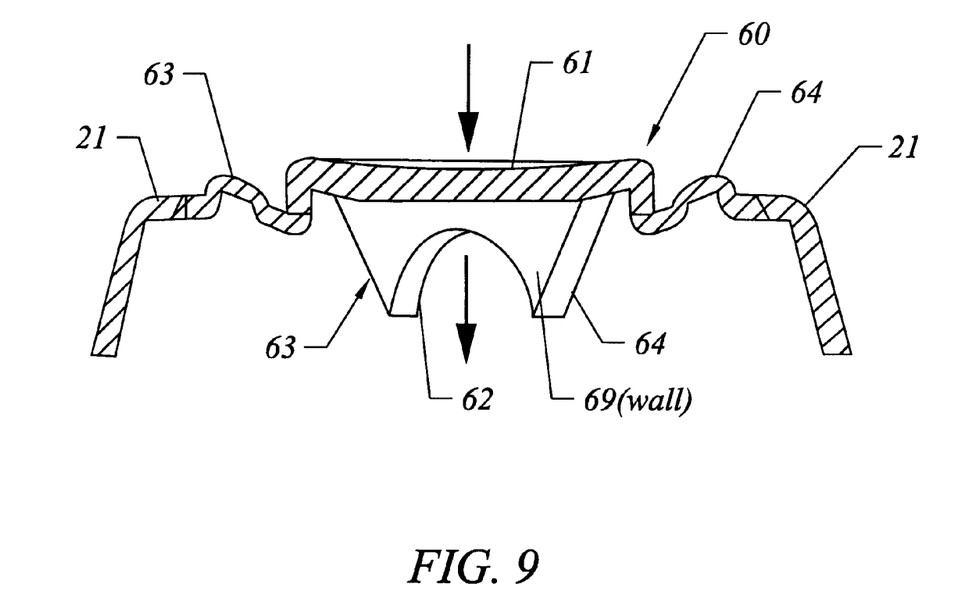
FIG. 9 is a schematic view of the trigger button as it is being depressed by the user.

FIGS. 8 and 9 shows schematically the operation of the trigger means shown generally as 60. Trigger button 61 is formed in the shape of a circular depression into the upper half 21 of the lancet. The trigger button 61 is connected to the upper body 21 solely by a plurality of generally S-shaped webs, two of which are shown in FIGS. 8 and 9 as 63 and 64. The use of the plurality of S-shaped webs to support button 61 allows the button 61 to be movable upwardly and downwardly relative to the body of the device. The preferred form of the invention as shown in FIG. 1 utilizes a total of four webs 63, 64, 65 and 66. Webs 63 and 64 are shown and described in FIGS. 8 and 9 and it is understood that webs 65 and 66 are identical and operate in the same fashion as webs 63 and 64. As the user depresses the trigger button 61, as shown in FIG. 9, S-shaped webs 63 and 64 deform and allow the button 61 to move downwardly relative to the upper half 21 of the device. Trigger button 61 projects above upper half 21 of body 20 approximately one millimeter to reduce the risk of accidental firing.

Trigger actuator shown generally as 68 in FIGS. 8 and 9 is essentially a vertical wall 69 molded onto the underside of trigger button 61. Vertical wall 69 includes an arcuate semi-circular surface 62 formed on its underside which allows passage of the needle assembly when the device is fired. The vertical wall 69 also includes inclined downwardly extending side walls 63 and 64. Side walls 63 and 64 form first and second actuators and extend downwardly at a angle of approximately 45° to the vertical with their surfaces 63 and 64 extending towards each other in the downward direction. These sloping side walls are utilized to separate the detent means 70 described below.

Figure 10:
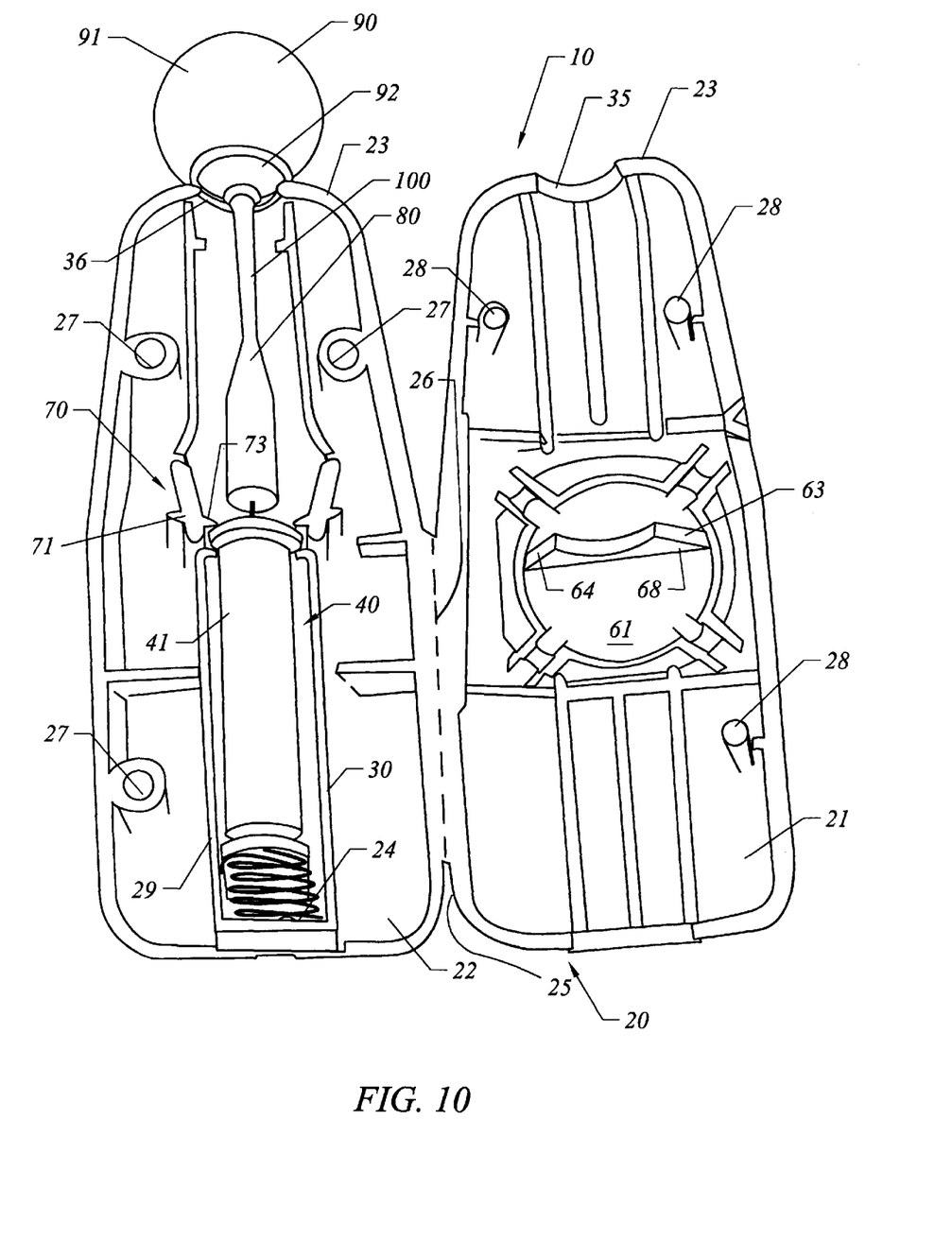
FIG. 10 is a perspective view showing the interior of the lancet with the needle assembly in its cocked position.

FIG. 10 shows the lancet 10 as fully assembled, precocked and ready to be closed for shipment. The upper half 21 of body 20 is flexibly joined to the lower half 22 of body 20 along one edge 25 which forms a hinge 26 shown as a dotted line. This hinging of the upper and lower body halves allows a clamshell opening and closing feature of the lancet. Three closure receptacles 27 are formed in the lower body half 22 and are adapted to receive closure pins 28 molded into the upper body half 21. Closure pins 28 extend into receptacles 27 when the halves are closed together.

The needle assembly 40 in its cocked position is held against seat 24 formed integrally in the lower half 22 of body 20. Seat 24 and side walls 29 and 30 form a guide for the needle assembly 40 as it moves from its cocked position shown in FIG. 10 to its striking position shown in FIG. 12. Detent means 70 holds needle assembly 40 in its cocked position and includes a pair of vertical projections 71 and 72 molded integrally into lower body half 22. Projections 71 and 72 extend vertically on either side of needle assembly 40 and include lugs 73 and 74 which extend toward needle assembly 40 and which engage the flange or collar 42 of needle carrier 41 and hold the needle assembly 40 securely in its cocked position. The vertical projections 71 and 72, and lugs 73 and 74, are robust and sufficiently large to reduce and prevent creep which would otherwise allow the lugs 73 and 74 to slowly separate and allow the needle assembly to fire prematurely.

FIG. 10 also shows the underside of trigger button 61 and shows the trigger actuator 68. The trigger actuator 68 engages the vertical projections 71 and 72 and, as the trigger button is depressed, the side walls 63 and 64 spread apart projections 71 and 72 and lugs 73 and 74, as shown best in FIG. 11.

Figure 11:
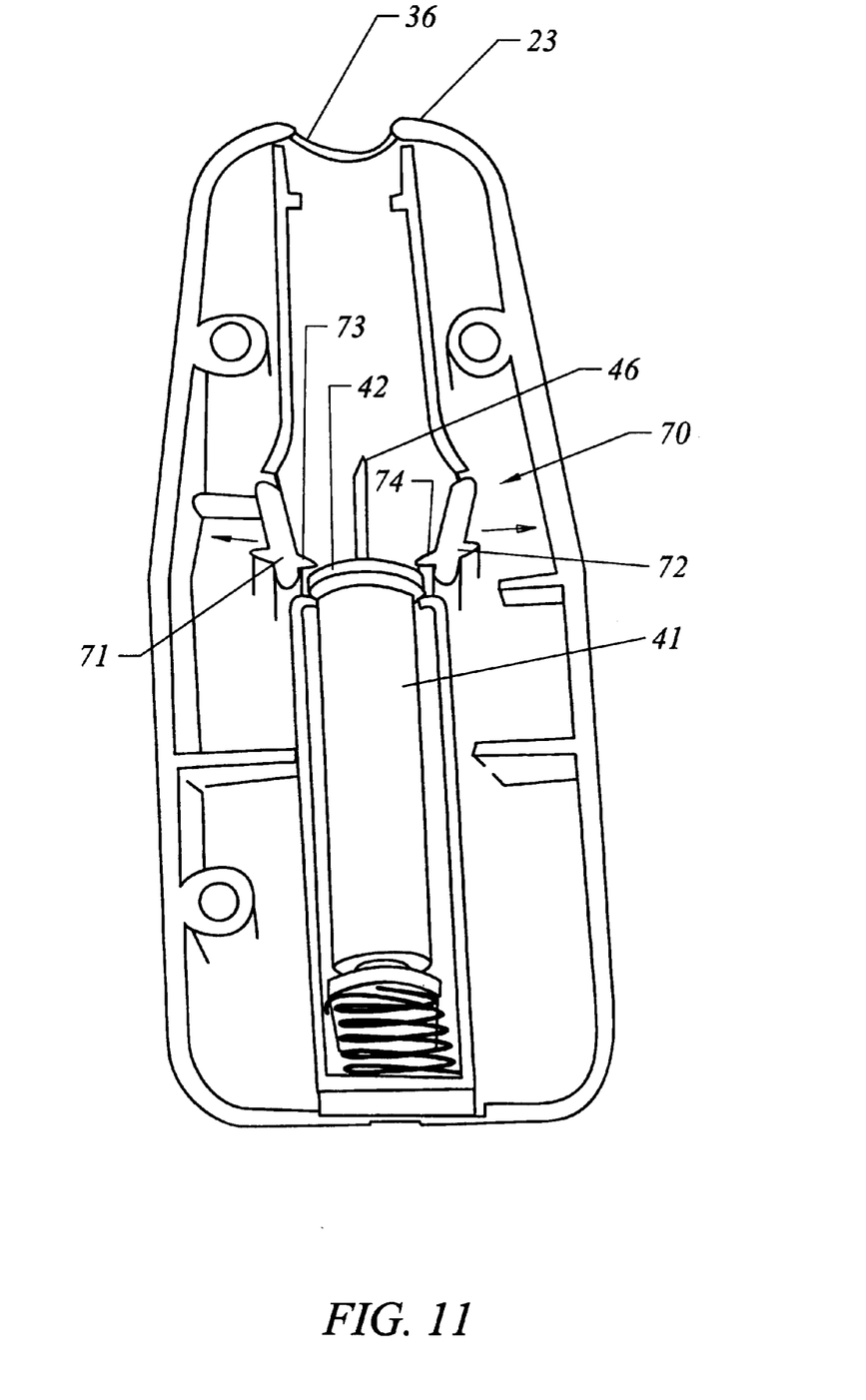
FIG. 11 is a perspective view of a portion of the lancet showing the manner in which the detent mechanism is momentarily deformed to release the needle assembly.

FIG. 11 shows the release of the detent means 70 by lugs 73 and 74 moving outwardly and away from needle assembly 40 in the direction of the arrows as the trigger button is depressed. Lugs 73 and 74 are moved outwardly from needle assembly a sufficient distance so that the collar or flange 42 of the carrier 41 is free to advance abruptly toward the striking position of the needle shown in FIG. 12.

Figure 12:
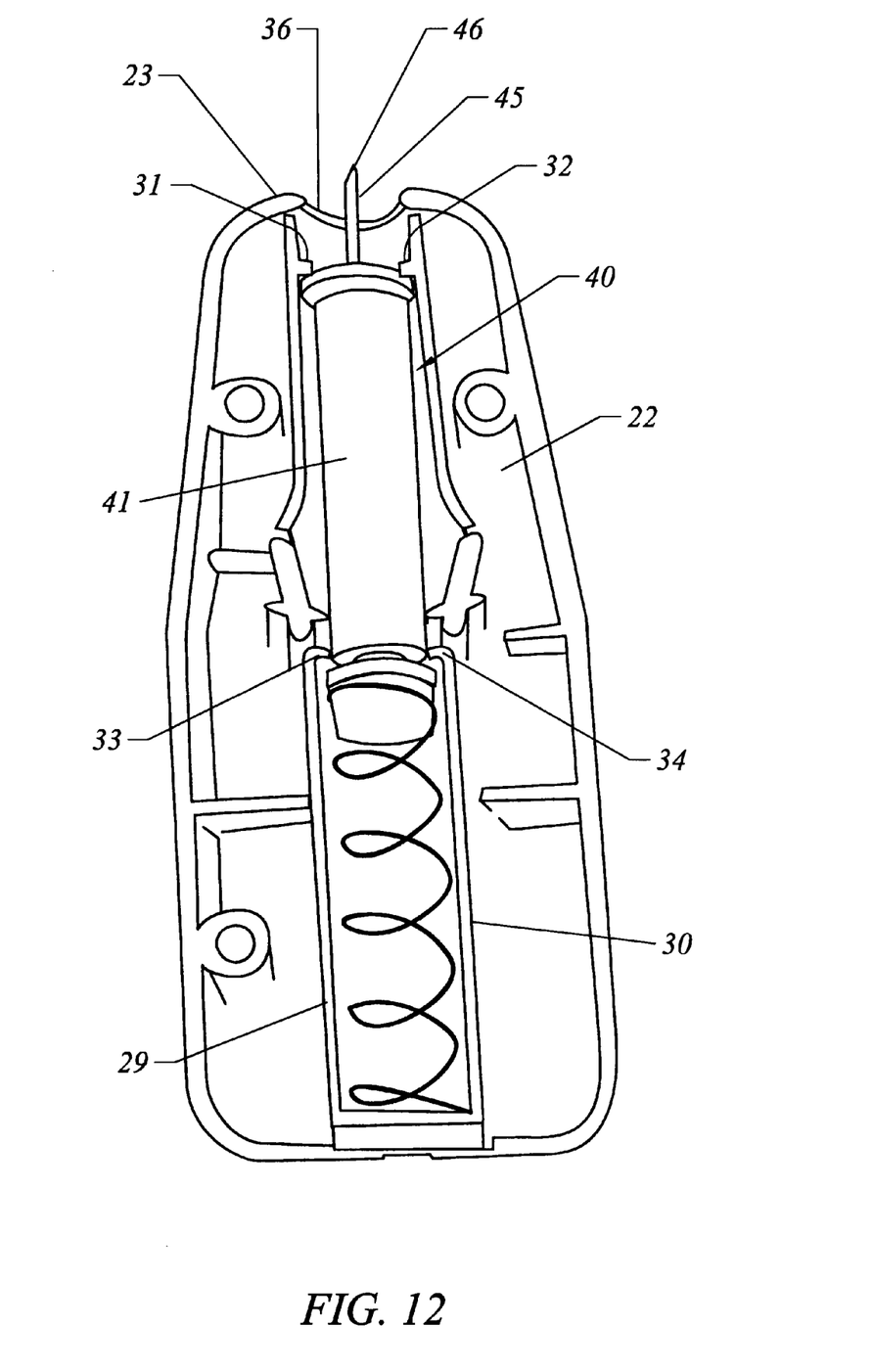
FIG. 12 is a perspective view of a portion of the invention showing the needle assembly in its striking position.
Figure 13:
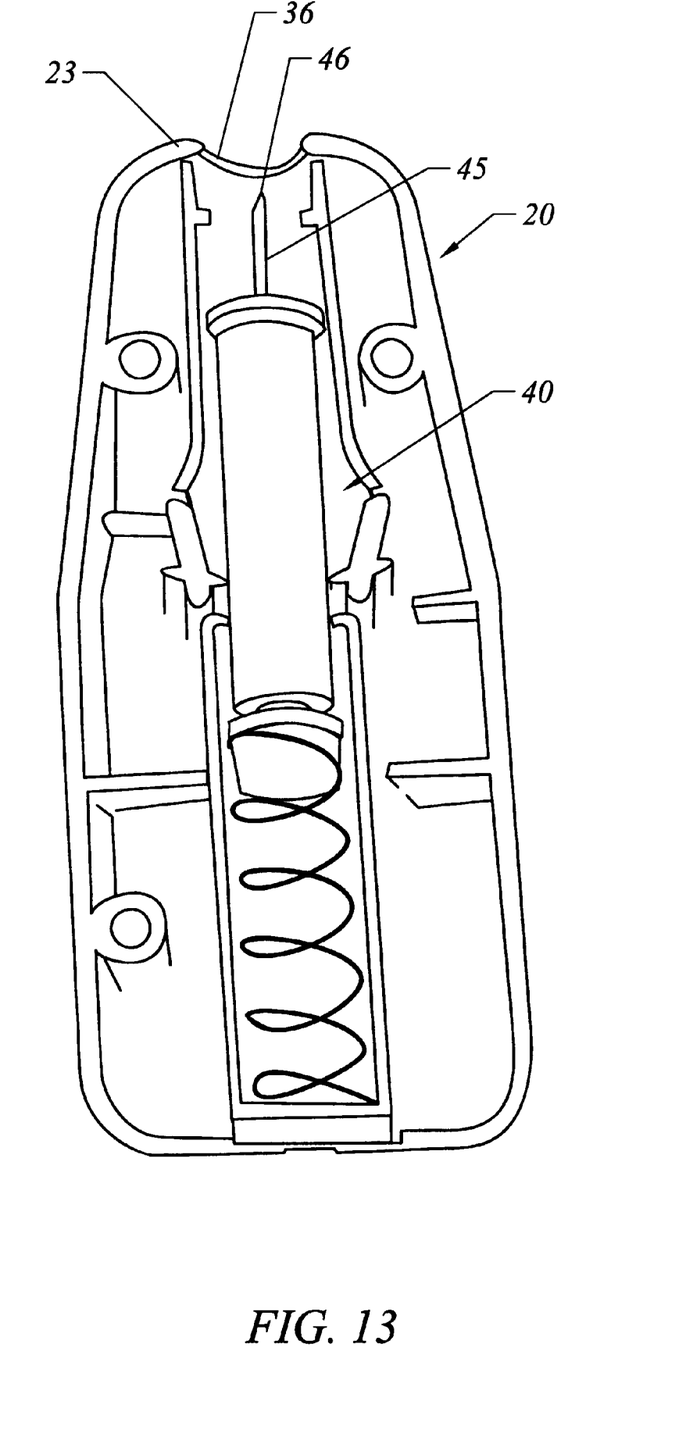
FIG. 13 is a perspective view showing a portion of the invention wherein the needle assembly is in its recoiled position, which is achieved shortly after its striking position.

Before the trigger is actuated, the pull-tab 90 and safety cap 80 as shown in FIG. 10 are removed as described above. FIG. 11 shows the pull-tab 90 and safety cap 80 removed and the needle tip 46 is exposed and ready to be advanced to its striking position. FIGS. 11–13 do not include the upper half 21 of the body 20 for clarity.

FIG. 12 shows the needle tip 46 and needle assembly 40 advanced to its outermost striking position. Forward stops 31 and 32 are formed integrally in the lower body half 22 and limit the depth of puncture created by needle 45 and its tip 46. Rear stops 33 and 34 are formed integrally at the forward end of walls 29 and 30 and serve to limit the forward motion of the carrier 41.

FIG. 13 shows the recoil position of needle assembly 40 in which the needle tip 46 is retracted back into the body 20 to reduce the likelihood of unintentional cuts or punctures. As shown in FIGS. 10–13, the forward end 23 of the device has a circular opening formed by semi-circular openings 35 and 36 formed in the upper and lower body halves 21 and 22, respectively. The opening formed by semi-circular recesses 35 and 36 is sufficient to allow the passage of safety cap 80.

As shown in FIG. 10, pull-tab 90 includes a rather large disc-shaped member 91 adapted to be grasped by a thumb and forefinger or to be pressed angularly by a fingertip as shown in FIGS. 2 and 3. Disc 91 is supported by a circular base 92, with base 92 extending generally perpendicularly to disc 91. The perpendicular orientation of disc 91 relative to base 92 allows the user to obtain a lever action by pressing or pulling disc 91 to the side, thereby causing the base 92 to exert leverage against the forward wall 23 of the body 20 and to assist in separating the safety cap 80 from the needle 45.

Figure 14A:
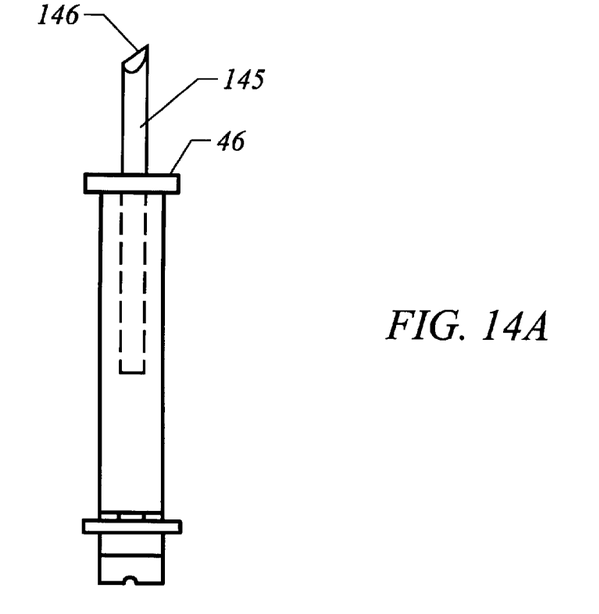
FIGS. 14A and 14B show chisel-tipped needles and bevel cut needles, respectively, capable of being used in the invention.
Figure 14B:
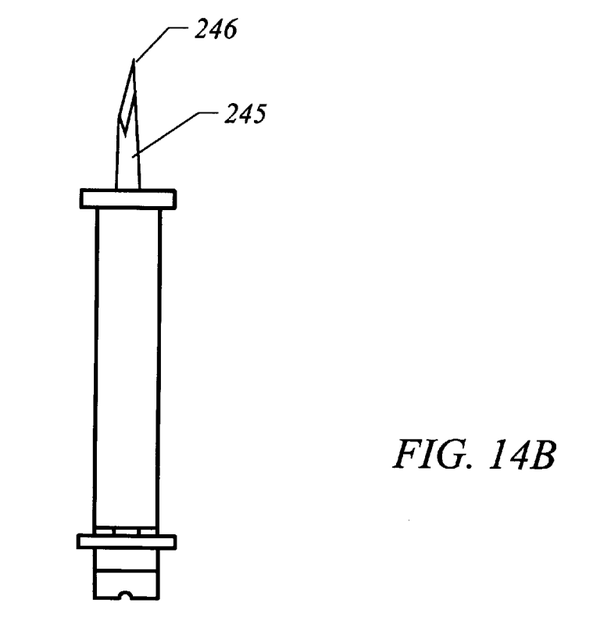

FIGS. 14A and 14B show two alternate needle tip designs that can be used with the lancet of the present invention. FIG. 14A shows a chisel-type needle 145, particularly useful in pediatric uses wherein a larger and shallower cut is made in the skin rather than a deeper and sharper puncture ordinarily preferred by adults. The tribevel cut needle 245 shown in FIG. 14B achieves a deeper puncture for use with adults.

What is claimed is:

1. A single-use disposable lancet comprised of:
   a trapezoidal or elliptically shaped body with upper and lower halves flexibly joined along one edge,
   a trigger button molded into the upper half of the body and capable of direct up and down motion,
   a needle assembly movable between a cocked position and a striking position,
   a drive spring for advancing said needle assembly,
   detent means for holding the needle assembly, said detent means being molded into the lower half of the body and released by downward motion of the trigger button,
   a detachable safety cap carried by said needle assembly which covers and protects the tip of said needle,
   a pull-tab extending outwardly from said body, and
   a thin plastic fiber connector between said pull-tab and said safety cap adapted to detach said safety cap when said pull-tab is manipulated, said thin plastic fiber connector being sufficiently flexible to prevent an effective compressive force from the pull-tab from being applied to the drive spring to recock said needle assembly.

2. The apparatus of claim 1 wherein the trigger button is molded with a vertical wall on its underside and where said vertical wall possesses an arcuate central surface to allow passage of the needle assembly and sloping sides positioned to activate said detent means molded into the lower body.

3. The apparatus of claim 1 wherein the lower body is molded with vertical projections which abut against a round collar on the needle assembly to hold it in a cocked position.

4. The apparatus of claim 1 whereby downward motion of the trigger button causes the sloping walls on its underside to spread apart vertical projections of the lower body, thereby releasing the drive spring and causing forward motion of the lancet.

5. The apparatus of claim 1 in which movement of the trigger button is enhanced by an "S" shape of the webs connecting the trigger button to the upper body.

6. The apparatus of claim 1 wherein said needle assembly includes a lancet carrier in which said needle is mounted, and further comprising a thin plastic connection between said pull-tab and the lancet carrier which prevents accidental displacement of said safety cap.

7. A single use, disposable and non-reusable lancet, comprising:
   a body,
   a needle assembly carried by said body, said needle assembly including a needle and a needle support,
   said needle assembly being movable between a cocked position and a striking position,
   a drive spring means for advancing said needle assembly from its cocked position to its striking position,
   detent means holding said needle assembly in its cocked position,
   trigger means for releasing said needle assembly from said detent means,
   a non-reusable, breakaway safety cap means for protecting and maintaining sterilization of said needle while in its cocked position,
   a pull-tab extending outwardly from said body, said pull-tab adapted to be grasped and manipulated by a user, and
   a thin flexible fiber connecting said safety cap and said pull-tab, whereby said pull-tab may be manipulated to cause said safety cap to separate from said needle assembly, and wherein said flexible fiber has insufficient compressive strength to recock said needle assembly.

8. The apparatus of claim 7 wherein said detent means includes first and second lugs positioned on opposite sides of said needle assembly, and wherein said trigger means is movable between a depressed firing position and a raised non-firing position, and wherein said trigger means includes first and second actuators that spread said first and second lugs in response to said trigger means being depressed.

9. The apparatus of claim 8 wherein said body is hinged along one side to allow said body to be opened in clamshell fashion, and wherein said needle assembly with said breakaway safety cap means is adapted to be precooked during manufacture.

10. The apparatus of claim 7 wherein said detent means is movable between a first position in which said detent means holds said needle assembly in its cocked position and a second position in which said needle assembly moves abruptly to its striking position.

11. The apparatus of claim 7 wherein said trigger means includes a concave depression adapted to comfortably receive a fingertip, and wherein said concave depression projects beyond the surface of said body approximately one millimeter to reduce the risk of accidental firing.

* * * * *

UNITED STATES PATENT AND TRADEMARK OFFICE
CERTIFICATE OF CORRECTION

PATENT NO. : 6,168,606
DATED : Paul D. Levin, et al.
INVENTOR(S) : January 2, 2001

It is certified that error appears in the above-identified patent and that said Letters Patent is hereby corrected as shown below:

The word "precooked" in the following places should be --- precocked ---

Abstract line 2;
    Column 1, lines 28, 32, 35
    Column 2, line 4
    Column 6, line 49

Signed and Sealed this

Tenth Day of July, 2001

*Attest:*

NICHOLAS P. GODICI
*Attesting Officer*      *Acting Director of the United States Patent and Trademark Office*